United States Patent [19]

Petro et al.

[11] Patent Number: 5,047,334

[45] Date of Patent: Sep. 10, 1991

[54] NOVEL PROKARYOTIC EXPRESSION AND SECRETION SYSTEM

[75] Inventors: Joan Petro, Cambridge; Jennifer Jackson, Reading; Scott Putney, Arlington, all of Mass.

[73] Assignee: Repligen Corporation, Cambridge, Mass.

[21] Appl. No.: 68,471

[22] Filed: Jun. 30, 1987

[51] Int. Cl.⁵ .................. C12N 15/31; C12N 15/70; C12N 15/03; C12P 21/00; C12P 21/02

[52] U.S. Cl. .................. 435/69.1; 435/69.7; 435/69.8; 435/68.8; 435/252.3; 435/252.33; 435/320.1; 536/27; 935/29; 935/48; 935/22; 935/73

[58] Field of Search .................. 435/68, 70, 71, 91, 435/172.1, 172.3, 252.3, 252.31–252.35, 320, 69.1, 69.7, 69.8, 71.2, 320.1; 536/27; 935/48, 29, 72, 73; 530/350, 825

[56] References Cited

PUBLICATIONS

Talmadge, K., Stahl, S. and Gilbert, W. (1980), "Eukaryotic Signal Sequence Transports Insulin Antigen in *Escherichia coli*", Proc. Natl. Acad. Sci. U.S.A., 77:3369–3373.

Masui, Y., Mizuno, T. and Inouye, M. (1984), "Novel High-Level Expression Cloning Vehicles: 10⁴-fold Amplification of *Escherichia coli* Minor Protein". Bio/-Technology, 2:81–85.

Ghrayeb, J., Kimura, H., Takahara, M., Hsuing, H. Masui, Y. and Inouye, M. (1984), "Secretion Cloning Vectors in *Escherichia coli*", EMBO J. 3:2437–2442.

Watson, M. E. E. (1984), "Compilation of Published Signal Sequences", Nucl. Acids Res., 12:5145–5164.

Chan, S. J., Weiss, J., Konrad, M., White, T., Bahl, C., Yu, S.-D., Marks, D. and Steiner, D. F. (1981). "Biosynthesis and Periplasmic Segregation of Human Proinsulin in *Escherichia coli*", Proc. Natl. Acad. Sci. U.S.A., 78:5401–5405.

Talmadge, K. and Gilbert, W. (1982), "Cellular Location Affects Protein Stability in *Escherichia coli*", Proc. Natl. Acad. Sci. U.S.A., 79:1830–1833.

*Primary Examiner*—James Martinell
*Attorney, Agent, or Firm*—Saliwanchik & Saliwanchik

[57] ABSTRACT

The subject invention concerns a novel and superior recombinant DNA expression/secretion system for use in prokaryotic organisms to produce useful proteins. The system can be used to have proteins secreted by an engineered prokaryotic host where normally the proteins are not secreted by the host. Also, when using the expression system, proteins are expressed at much higher levels than when the expression system is not used.

16 Claims, 2 Drawing Sheets

NOVEL PROKARYOTIC EXPRESSION AND SECRETION SYSTEM

DESCRIPTION

Background of the Invention

Recombinant DNA methodology is being used to prepare proteins which are useful as industrial enzymes and medicines. The efficient production of these proteins is dependent upon many factors, for example, the construction of the "microbial factory," and the conditions under which the microbe produces the desired protein. In the construction of the microbial factory, it has been found that certain DNA sequences can be employed, advantageously, to enhance the level of production of the desired protein. These production enhancers, generally referred to as "promoters," are of many types. Some commonly-used promoters are lac, gal, and trp. Using recombinant DNA procedures, the promoter DNA is inserted in front of the gene encoding the desired protein which is contained in a vector, for example, a plasmid. The vector is then used to transform cells, for example, a microbial host. Upon culturing the transformed cell there are produced enhanced levels of protein as compared to the levels produced by cells not containing a strong, or enhancing type, promoter.

*Escherichia coli* is an important host organism for the expression of cloned genes and the purification of recombinant enzymes. Several gene promoters have been identified that direct high level expression of foreign genes in *E. coli*. Most of the expression systems in use cause the cloned gene product to accumulate in the cytoplasm. Through the use of protein signal sequences, foreign gene products can be secreted out of the cytoplasm into the periplasmic space between the *E. coli* inner and outer membranes (Talmadge, K., Stahl, S. and Gilbert, W. [1980] Proc. Natl. Acad. Sci. USA 77:3369-3373; Masui, Y., Mizuno, T. and Inouye, M. [1984] Biotechnology 2:81-85; Ghrayeb, J., Kimura, H., Takahara, M., Hsiung, H., Masui, Y. and Inouye, M. [1984] EMBO J. 3:2437-2442).

There are several potential advantages to having a cloned gene product secreted into the periplasmic space, including: 1) The protein product can avoid cytoplasmic proteases; 2) normally secreted proteins such as hormones, ligninolytic enzymes, and dextranases may only be able to fold in their active conformation in *E. coli* if secreted; 3) toxic enzymes such as nucleases or proteases cannot be produced in the cytoplasm or they will kill the cell; and 4) ease of purification. There are well known methods for isolation of periplasmic proteins, which normally comprise only 4% of cellular protein.

The signal sequence, or leader peptide, is found in precursors of most secreted proteins in bacteria and in eukaryotes, and is used to direct the secreted protein to its proper cellular location. Signal sequences, though generally structurally related, have little sequence homology even between secreted proteins in the same organism (Watson, M. E. E. [1984] Nucl. Acids Res. 12:5145-5164). However, signal sequences do appear to be functionally similar. For example, mammalian proinsulin can be secreted into the periplasmic space in *E. coli* when preceded by its own eukaryotic signal sequence or the bacterial beta-lactamase signal sequence. (Chan, S. J., Weiss, J., Konrad, M., White, T., Bahl, C., Yu, W. D., Marks, D. and Steiner, D. F. [1981] Proc. Natl. Acad. Sci. USA 78:5401-5405; Talmadge, K. and Gilbert, W. [1982] Proc. Natl. Acad. Sci. USA 79:1980-1833).

A high level *E. coli* expression secretion vector, pIN-III-ompA, has been described that is based on the lpp promoter and the ompA signal peptide (Ghrayeb, J. et al. supra). The primary recombinant gene product contains the ompA signal sequence, which directs the protein to be secreted across the cytoplasmic membrane into the periplasm. As the gene product is secreted across the membrane, the signal sequence is cleaved to release the processed protein into the periplasm.

At this time in the art, there is still a need for better promoters and/or secretion systems. The continued discovery of new promoters and secretion systems will make possible more efficient production of desirable proteins via recombinant DNA procedures.

BRIEF SUMMARY OF THE INVENTION

The subject invention concerns a novel and superior prokaryotic expression and secretion system. The expression system of the invention can be used to enhance, advantageously, the expression of a desired protein by an engineered microbe. More specifically, the DNA expression system of the invention can be inserted in front of a gene encoding a desired protein which is contained in a plasmid. The plasmid vector then can be used to transform a microbial host which, when cultured under suitable conditions, would then produce high levels of the desired protein.

Still more specifically, the present invention relates to the discovery and use of a previously unidentified *E. coli* DNA sequence, hereafter called NP949, in an expression system for cloned genes in bacteria. The DNA sequence has two major functional regions: (i) a control region or promoter, and (ii) a protein secretion signal sequence. The NP949 promoter and signal sequence can be used separately or together by a person skilled in the art to direct high level production and/or secretion of a cloned gene product in bacteria. The control region includes sequences that allow the expression of foreign gene products to be regulated by the inclusion of different carbon sources in the growth media.

Expression vectors which exemplify the subject high expression and secretion system are hybrid plasmids pNP949 and pNP949H. Novel hybrid plasmid pNP949 contains approximately 6.3 kb of previously unidentified *E. coli* DNA in the BamHI site of the known plasmid pUC12. Novel hybrid plasmid pNP949H was constructed by cutting plasmid pNP949 with HindIII and religating the resultant 6.2 kb fragment containing 2.7 kb of pUC12 DNA and 3.5 kb of insert DNA.

BRIEF DESCRIPTION OF THE DRAWINGS AND OF CHARTS A AND B

FIG. 2—Plasmid pNP949H was constructed by ligating the 6.2 kb HindIII fragment of pNP949. CHART A—Disclosed is the nucleotide sequence of 1773 base pairs of DNA from pNP949 extending from the SmaI site past the PstI sites. Also included is the corresponding protein sequence of the first 251 amino acids of NP949. The signal sequence is underlined. Restriction endonuclease sites are labeled above the nucleotide sequence. RBS is the ribosome binding site.

CHART B—DNA sequence which, when used in a prokaryotic expression system, confers extremely high expression and secretion activity.

DETAILED DESCRIPTION OF THE INVENTION

The NP949 gene, including the promoter and signal sequence, was isolated from a random library of *E. coli* DNA cloned into commercially available plasmid pUC12. Recombinant plasmids from this library were screened by SDS-PAGE for their ability to direct the expression of a large amount of any single protein. Plasmid pNP949 directed the expression of two novel proteins of approximately 57 and 60 kilodaltons (kd) at levels ranging from 20-50% of total cellular protein. A computer-aided search for amino acid homology in the NBRF, New NBRF, and NEWAT protein sequence data banks, containing 4235, 497, and 1246 protein sequences, respectively, has not identified this protein.

Materials and Methods

1) Media

Cultures were grown in YT medium (8 gm tryptone, 5 gm yeast extract, 5 gm NaCl/L) or modified 2% medium (20 gm yeast extract, 20 gm tryptone, 20 gm casamino acids, 2 gm $KH_2PO_4$, 2 gm $K_2HPO_4$, 2 gm $Na_2HPO_4$/L). Ampicillin was added to 50 μg/ml as required. Glucose and glycerol were added to 1%. Plates contained 1.5% agar. Plasmid screening plates contained 50 μg/ml ampicillin, 1 mM isopropylthiogalactoside (IPTG) and 0.01% 5-bromo-4-chloryl-3-indolyl-β-D-galactopyranoside (XGal). Alkaline phosphatase screening plates contained 0.01% 5-bromo-4-chloro-3-indolyl-phosphate (XPhos).

2) Chemicals and Reagents

Growth media components were obtained from Difco (Detroit, MI). Restriction enzymes and ligase were obtained from New England Biolabs (Beverly, MA). Acrylamide, bis-acrylamide, TEMED and SDS were obtained from International Biotechnologies, Inc. (New Haven, CT). All other chemicals were obtained from Sigma Chemical Company (St. Louis, MO).

3) *E. coli* DNA

*E. coli* DNA was prepared from strain MS371 essentially according to Marmur (1961, J. Mol. Biol. 3:208-218) with modifications of Anilionis and Riley (1980, J. Bacteriol. 143:355-365). All *E. coli* strains disclosed herein are *E. coli* K-12 derivatives.

4) Plasmid DNA Preparation

Procedure used for large scale preparation of plasmid DNA was essentially as follows: A 500 ml culture was grown overnight. Cells were pelleted at 6K, 20 min, JA14 rotor (Beckman Instruments, Inc., Palo Alto, CA) and resuspended in 6 ml glucose buffer (50 mM glucose, 25 mM tris, 10 mM ethylenediaminetetraacetic acid [EDTA]). Cells were incubated 10 min at room temperature in the presence of 1 ml of 20 mg/ml lysozyme freshly made; placed on ice with the addition of 13.8 ml 1% SDS in 0.2 N NaOH for 5 min, and kept on ice an additional 15 min with 7 ml 5M potassium acetate (KAC) (pH 5.0-5.5). Debris was pelleted twice at 12K for 20 min and supernate extracted once with an equal volume of phenol (TE [10 mM tris, 1 mM EDTA pH 8] saturated) and once with an equal volume of chloroform. Following precipitation with 0.6 vol isopropyl alcohol, DNA was purified over CsCl/EtBr gradients.

Procedures used for small scale preparation of plasmid DNA was essentially as described by T. Maniatis, E. F. Fritsch and J. Sambrook in *Molecular Cloning, A Laboratory Manual*, page 368-369, Cold Spring Harbor, 1982.

5) Restriction Enzyme Digestion, Agarose Electrophoresis, and Isolation of Desired Fragments Digestions were carried out according to suppliers' instructions.

DNA fragments were isolated by gel electrophoresis in 0.8% agarose in 2X TBE (178 mM tris, 178 mM boric acid, 4 mM $Na_2EDTA$ pH 8). Analytical and preparative gels were run in a horizontal gel box at 100 volts submerged in electrophoresis buffer (2X TBE). DNA bands were visualized under UV light by including 0.5 μg/ml ethidium bromide (EtBr) in the gel. A slice containing the desired DNA band was cut from the gel and the DNA recovered by electrophoresis in ½X TBE in a dialysis tube (½ in diameter) containing 0.5-1.0 ml of buffer. Electrophoresis was carried out for 1 hr at 100 volts or until the stained material was located against the side of the dialysis tubing, followed by a reversal of current for 1 min to decrease adherence of the DNA to the dialysis tubing. The gel slice was removed from the dialysis bag and the DNA recovered by repeatedly flushing the bag with ½x TBE. Eluted DNA was purified and concentrated by passing over Elu-tip columns (Schleicher and Schuell, Keene, NH) according to supplier's instructions, followed by precipitation in 2.5 volumes EtOH. The precipitation reaction was carried out at −70° C. for 15-20 min. The precipitated DNA was recovered by centrifugation at 10,000 x g for 15 min. Yield of recovered fragment was assayed by direct comparison of ethidium bromide fluorescence with pure DNA standards. Typically, 50% recoveries were obtained, with the yield decreasing as fragment size increased.

6) DNA Ligations

T4 DNA ligase was used for standard vector/insert ligations and was present in excess (200 u/μg DNA); insert was present in a 5-fold molar excess with 0.02 pmol of vector and 0.1 pmol of insert in a 10 μl reaction volume.

7) Transformation

Fresh overnight cultures were diluted in YT medium and allowed to grow at 37° C. with agitation until an $A_{600}$ of 0.3 was obtained. The cells were chilled on ice, then collected by centrifugation (10 min at 4100 x g). The cells were resuspended in ½ the original volume of ice cold 50 mM $CaCl_2$ and incubated on ice for 20 min. The cells were again collected by centrifugation as above and resuspended in ice cold 50 mM $CaCl_2$ (1/25 the original volume). 0.1 ml of the cell suspension was mixed with 1-10 μl (1-10 ng) of DNA plasmid solution and incubated for 30 min at 0° C. The cells were then heated to 42° C. for 2 min and plated on YT plates containing 1.5% agar and appropriate selective and/or screening solutions. The plates were incubated overnight at 37° C. Transformation efficiencies of $1 \times 10^6$ colonies per μg plasmid DNA were routinely observed.

8) DNA Sequencing

DNA sequence determination was carried out as described by Sanger, F., Nicklens, S. and Coulson, A. R. (1977) Proc. Natl. Acad. Sci. USA 74:5463-5467.

9) Polyacrylamide Gel Electrophoresis

All SDS gels were run and stained by the method of Laemmli (Laemmli, U.K. [1970] Nature [London] 227: 680-685). These gels contained a total acrylamide concentration of 9%. Slab gels were 1.5 mm wide, run in a MIGHTY SMALL ™ electrophoretic apparatus obtained from Hoefer Scientific Instruments (San Francisco, CA).

10) Alkaline Phosphatase Assays

Alkaline phosphatase assays were performed essentially as described by A. Torriani (1966) in *Procedures in Nucleic Acid Research*, eds. Cantoni, C. L. and Davies, D. R., Harper and Row, New York, NY, pp. 224-235.

11) β-galactosidase Assays

β-galactosidase assays were performed essentially as described by J. H. Miller (1972) in *Experiments in Molecular Genetics*, Cold Springs Harbor Laboratory, Cold Springs Harbor, NY, pp. 398-404.

12) *E. coli* Bacterial Strains

| Strains | Relevant Genotype |
|---|---|
| JM103 (NRRL B-39403) | F+ traD36, proAB, lacIqZM15 Δ(lac,pro), supE, thi, strA, endA, sbcB15, hsdR4 |
| KL386 | F− recAl, srl, leu$^{-6}$, metE70, str-109, supD$^-$, nalA', lacI3, lacZ118, ara-14, xyl-5, mtl-1 |
| MS371 | F− gal$^-$, thi, end A, sbc B, hsd R4, hsd M$^+$ |

13) Deposited Cultures

The cultures disclosed below have been deposited in the Agricultural Research Service Patent Culture Collection (NRRL), Northern Regional Research Center, 1815 North University Street, Peoria, Il. 61604, USA.

| Strain | Plasmid | Repository Number | Date of Deposit |
|---|---|---|---|
| KL386 | pNP949 | NRRL B-18231 | June 18, 1987 |
| KL386 | pNP949H | NRRL B-18232 | June 18, 1987 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them. 14) Construction of Hybrid Plasmids The source for the DNA used to construct hybrid plasmid pNP949 was *E. coli* MS371. This DNA was inserted into the BamH1 site of pUC12. Ligation mixtures were transformed into competent cells of *E. coli*. Subsequent plating on YT agar, followed by screening and purification, yielded a clone designated NP949. Plasmid DNA was isolated from this clone and retransformed. The identity of plasmid pNP949 was then established by size of DNA, restriction endonuclease pattern and expression and secretion of the plasmid encoded 57 and 60 kd proteins in prokaryotic host.

Novel hybrid plasmid, pNP949H was constructed from plasmid pNP949 by taking the 6.2 kb HindIII fragment of pNP949 and religating it. The identity of pNP949H was established as above for pNP949. 15) Isolation of Host Transformed with a Plasmid The host microbe, e.g., *E. coli* KL386, can be recovered minus the plasmid, e.g., pNP949 or pNP949H, with which it was transformed, by standard procedures. For example, the transformed host can be grown in YT medium containing 0.01% w/v SDS to eject the plasmid from the host. Host cells without plasmid can be screened because of the loss of resistance to chloramphenicol and/or ampicillin.

Following are examples which illustrate the process of the invention, including the best mode. These examples should not be construed as limiting. All solvent mixture proportions are by volume unless otherwise noted.

EXAMPLE 1

Preparation of libray of random fragments of *E. coli* DNa from strain MS371 in plasmid pUC12

150 μg of MS371 DNA were incubated at 37° C. with 0.027 u Sau 3A/μg DNA in a reaction volume of 150 μl. After 30 min incubation, the reaction was stopped and the reaction mixture was electrophoresed through a 0.7% agarose gel. The gel region containing DNA fragments of 5 to 7 kb was excised and the DNA electroeluted from the gel slice. The electroeluted DNA sample was cleaned of agarose and other impurities by passing over an Elutip column (Schleicher and Schuell, Keene, New Hampshire). The column-eluted DNA was precipitated by the addition of 3 volumes ethanol, incubation at −70° C. for 30 min and centrifugation at 10,000 x g for 15 min. DNA yield was determined by direct comparison of ethidium bromide fluorescence with pure DNA standards. 0.1 pmol of MS371 DNA fragments was ligated with 0.02 pmol BamHI cleaved pUC12 (P-L Biochemicals, Milwaukee, WI) in a total volume of 10 μl at 16° C. for 2-4 hr. The ligation mixture was transformed into competent cell of *E. coli* strain JM103 and spread over YT agar plates supplemented with 50 μg/ml ampicillin, 1.0 mM IPTG and 0.01% XGal. The plates were incubated at 37° C. for 14-18 hr. Under these conditions pUC12 will give rise to blue colonies and pUC12 with inserted DNA will give rise to white colonies.

EXAMPLE 2

Screening the DNA library to obtain pNP949 which overexpresses a novel protein

Two ml of modified 2% medium supplemented with 50 μg/ml ampicillin were inoculated with a transformant colony containing a recombinant plasmid from the random DNA library. The culture was incubated at 37° C. with agitation for 14–18 hr and then assayed by SDS-PAGE. Of the 1,500 transformants analyzed, 81, or 5.4%, produced a plasmid-encoded protein as 5% or greater of total cellular protein.

Clone NP949 expressed two proteins of approximate molecular weight 57–60 kd at 20–50% of cellular protein. Isolation of pNP949 plasmid DNA and retransformation into E. coli strain KL386 showed that the high protein expression was encoded by the plasmid.

EXAMPLE 3

Identification of the product of the NP949 gene as a secreted protein

Cultures of strain KL386 containing plasmid pNP949 overexpress two closely migrating proteins of approximate molecular weight 57–60 kd. The relative amounts of the two proteins varied with host strain and culture conditions. Cell fractionation studies indicate that the higher molecular weight species is membrane associated and the lower molecular weight protein is secreted into the periplasmic space.

Periplasmic proteins were separated from cytoplasmic proteins by the lysozyme-EDTA method of Malamy, M. H. and Horecker, B. L. (1964) Biochemistry 3:1889–1892, or by osmotic shock as follows. E. coli cells were harvested by centrifuging 300 μl of culture at 10,000×g for 2 min. Pelleted cells were resuspended in 300 μl 20% sucrose, 10 mM Tris, pH 8.0 with 10 μl 0.5 M EDTA pH 8.0 and incubated for 10 min. 50 μl of this mixture was removed as the untreated control. The remainder was centrifuged at 10,000×g for 2 min. The pelleted cells were vigorously resuspended in 250 μl 0° C. H$_2$O and incubated on ice for 10 min. The released periplasmic proteins were separated from the cytoplasmic proteins by centrifuging at 10,000×g for 5 min. Cytoplasmic proteins were resuspended in an equal volume of H$_2$O. Efficiency of fractionation was monitored by alkaline phosphatase and β-galactosidase assays.

A precursor-product relationship between the two highly expressed proteins is indicated by two facts. First, the DNA sequence NP949 (Chart A) shows a canonical secretion signal sequence that would produce a precursor protein of approximate molecular weight 2.3 kd greater than the mature protein. Second, a gene fusion using the 340 bp NlaIII fragment of pNP949 coding only for the upstream promoter region and signal sequence directs the high-level expression of the E. coli alkaline phosphatase gene (see below) as two proteins that differ by the same approximately 3 kd as the two proteins expressed by the NP949 gene alone. The NP949 gene was shown to be subject to catabolite repression. Growth of clone NP949 in medium containing 1% glucose effectively stopped high protein expression as assayed by SDS-PAGE. Growth in medium containing 1% glycerol allowed over-expression of gene NP949.

EXAMPLE 4

Identification of the DNA sequence necessary for the high expression and secretion of protein NP949

Figure 1:
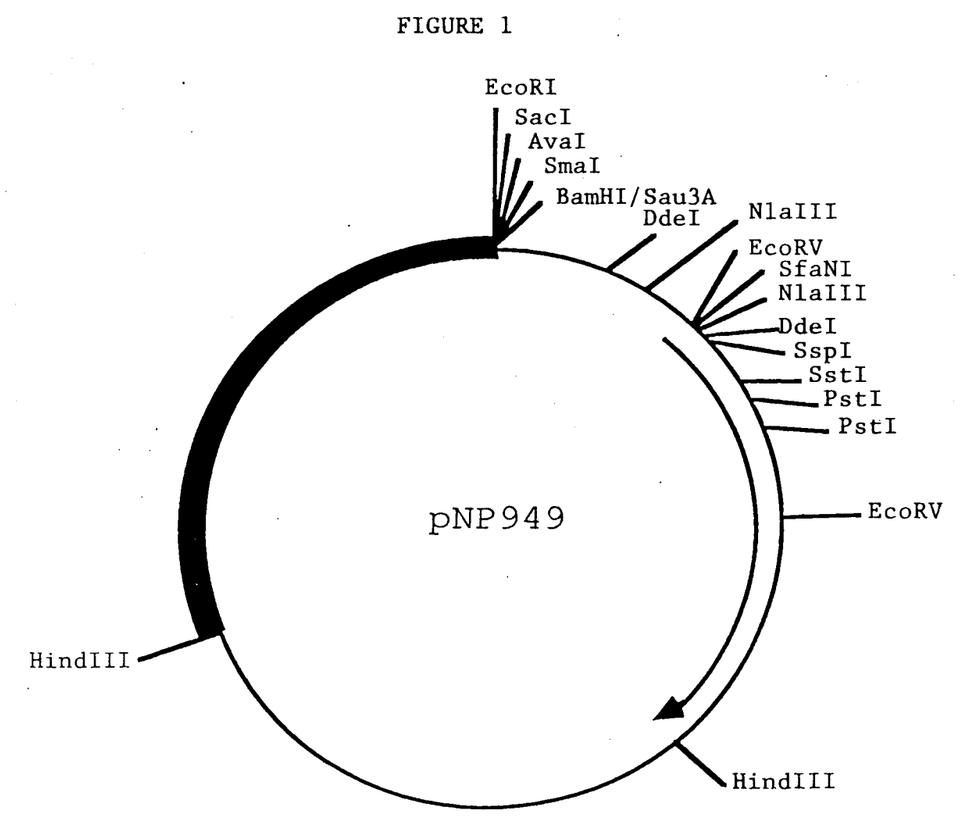
FIG. 1—A restriction site map of plasmid pNP949 was derived by standard methods. The thick arc represents pUC12. The thin arc represents the 6.3 kb of MS371 DNA. The arrow indicates the NP949 gene.

A map of the restriction enzyme sites in plasmid pNP949 is shown in FIG. 1. The E. coli DNA insert from strain MS371 is 6.3 kb long. Plasmid pNP949H (FIG. 2) was constructed by cutting plasmid pNP949 with HindIII and religating the resultant 6.2 kb fragment containing 2.7 kb of pUC12 DNA and 3.5 kb of insert DNA. Plasmids pNP949 and pNP949H were transformed into strain KL386 and the total protein content of overnight cultures of these transformants was shown to be identical by SDS-PAGE. Thus, the 3.5 kb of insert DNA in plasmid pNP949H is sufficient to code for protein NP949.

Figure 2:
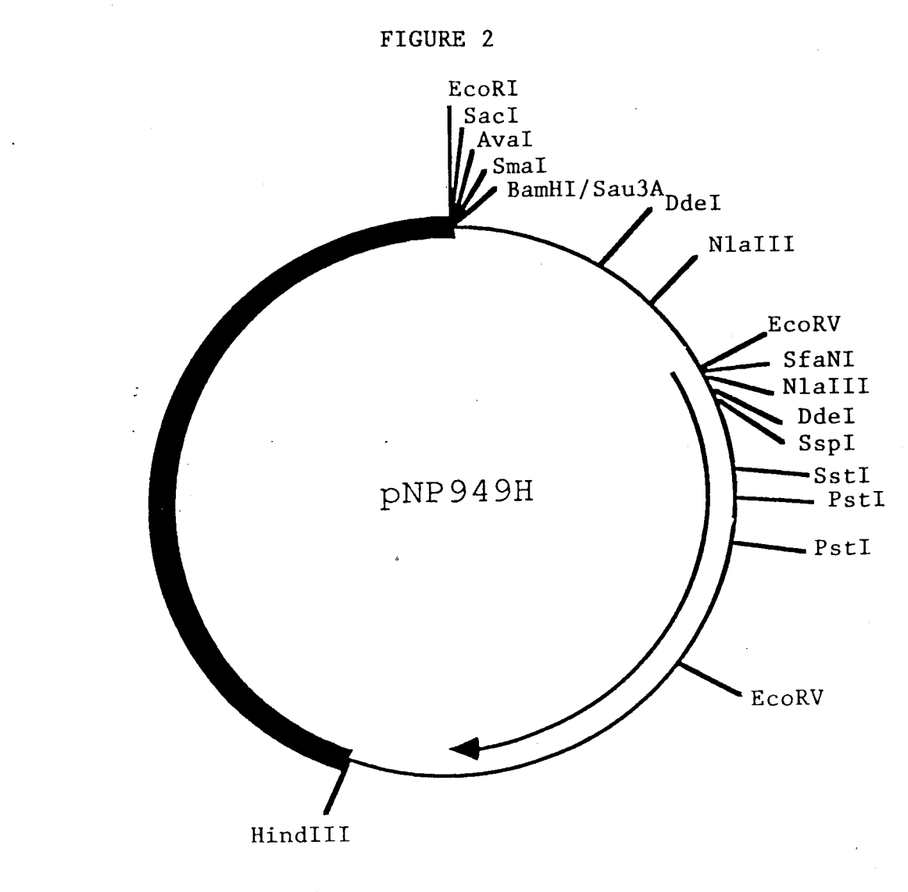

Chart A shows the sequence of 1773 bp of the pNP949 E. coli DNA insert, extending from the SmaI site past the two PstI sites shown in FIGS. 1 and 2. Computer aided searches of the DNA sequence of the NP949 gene upstream control region reveal a potential promoter configuration, a presumptive CAP binding site, and a strong ribosome binding site with an appropriately spaced methionyl initiator codon. Downstream from the methionyl initiator codon is a canonical secretion signal sequence (Oliver, D. [1985]Ann. Rev. Microbiol. 390:615–648).

The DNA sequences of the invention can be utilized to express heterologous proteins in several forms: 1) An operon fusion can be constructed by splicing the control region of NP949 to the structural gene for the desired product between the promoter and methionyl initiator codon of NP949. An operon fusion directs the expression of the desired gene product without additional vector-derived N-terminal amino acids. The gene product of an operon fusion will remain in the cytoplasm. 2) Splicing between the methionyl initiator codon and the predicted signal sequence cleavage site will result in the expression of a hybrid protein that will also accumulate in the cytoplasm. 3) Joining of foreign DNA to NP949 downstream of the signal sequence cleavage site can result in the secretion of a heterologous protein. The N-terminal sequence of the resulting secreted protein will depend upon how close the join is to the cleavage site. Oligonucleotide mutagenesis could be used to delete any extraneous sequences between the cleavage site and the heterologous protein coding sequences to yield a secreted protein with natural N-terminal sequence.

In the examples which follow, the NP949 control region and gene have been used to direct the expression of alkaline phosphatase as a nonsecreted hybrid protein, as a secreted nonhybrid protein, and as secreted hybrid proteins. Alkaline phosphatase is a good model protein to test the usefulness of the NP949 expression secretion system because this enzyme is only active when secreted into the periplasmic space (Michaelis, S., Inouye, H., Oliver, D. and Beckwith, J. [1983] J. Bacteriol. 154:366–374). Alkaline phosphatase activity in a transformed clone causes colonies grown on agar plates containing XPhos to turn blue and thus can be rapidly and easily ascertained.

EXAMPLE 5

A nonsecreted hybrid protein was expressed by a recombinant plasmid in which the structural gene of E. coli alkaline phosphatase (phoA) was spliced to the NP949 control region at the NP949 SfaNI. The phoA structural gene which lacked its own control region and signal sequence was contained on the 3.3 kb PstI fragment of plasmid pCH2 (Hoffman, C. S. and Wright, A. [1985] Proc. Natl. Acad. Sci. USA 82:5107-5111). SfaNI cleaves the NP949 gene at nucleotide number 1088, which is between the initiator methionyl codon and the signal sequence processing site as shown in Chart A. The hybrid protein resulting from fusion at the SfaNI site was expressed as 10% of total cellular protein. Alkaline phosphatase activity was not detected on XPhos agar plates. The hybrid alkaline phosphatase was shown to be located in the cytoplasm by cell fractionation and SDS-PAGE analysis.

EXAMPLE 6

A secreted hybrid protein was expressed by a recombinant plasmid in which the *E. coli* alkaline phosphatase gene was spliced to the NP949 gene at the NP949 DdeI site. As shown in Chart A, DdeI cleaves the NP949 gene at nucleotide number 1152, which is 18 codons downstream of the putative signal sequence processing site. The hybrid alkaline phosphatase resulting from the DdeI fusion was expressed as approximately 25% of total protein and was active. Cell fractionation and SDS-PAGE analysis showed the hybrid protein to be secreted to the periplasmic space.

EXAMPLE 7

A secreted nonhybrid protein was expressed by a recombinant plasmid in which the alkaline phosphatase gene was spliced to the NP949 gene at the NP949 NlaIII site. NlaIII cleaves the NP949 gene at nucleotide number 1101, which is only one codon downstream of the putative signal sequence processing site. The presumably native alkaline phosphatase resulting from the NlaIII fusion was expressed as approximately 20% of the cellular protein and was active. The protein was secreted to the periplasm as shown by cell fractionation and SDS-PAGE analysis.

NP949 and the secreted alkaline phosphatase fusion proteins are expressed as both unprocessed, unsecreted precursor and processed, secreted product. The relative amounts of each form varies in a host strain-dependent manner. The two forms are easily purified away from each other, as they exist in separate cellular compartments, the precursor being in the cytoplasm and the processed product in the periplasmic space. There are well-known methods for isolation of both periplasmic and cytoplasmic proteins.

Since plasmid pNP949H carries all the sequences necessary for high expression and secretion, it can be used as a transfer vector for the expression and/or secretion of useful proteins, as discussed previously. The procedures for use of the nucleotide sequence of NP949 shown in Chart A to function as a signal sequence in a variety of transfer vectors and prokaryotic hosts are well known and standard in the art. For example, the signal sequence of Chart A can be used in much the same manner as the ompA signal sequence is presently used in the art. Further, it has been determined that only a portion of the nucleotide sequence shown in Chart A is sufficient to produce a very high level of expression and secretion (10-40% of total cellular protein) of a heterologous protein (alkaline phosphatase) in a prokaryotic (*E. coli*) expression system. We have shown that the sequence in Chart B confers extremely high expression and secreting activity.

The NP949 sequence can also be used as a transfer vector for the expression of other useful proteins. There are well known and standard procedures for use of the DNA sequence of pNP949 shown in Chart A as a promoter in a variety of prokaryotic hosts. For example, an operon fusion can be made by splicing at the MboII site at nucleotide number 1007 or at any other site between the promoter and the initiator methionyl codon. Also, a hybrid protein can be expressed by prokaryotic cells carrying a plasmid in which the structural gene of the desired protein is spliced to NP949 DNA between the initiator methionyl codon and the predicted signal sequence processing site. The EcoRV site at 1059 or the SfaNI site at 1088 are convenient splice sites for a protein fusion.

The nucleotide sequences disclosed herein can be readily engineered by a person skilled in the art so that any part of the sequence can be used in an expression and/or secretion system to enhance the production of useful proteins. For example, the sequence can be cut at any one of the restriction sites shown, and at others not shown, to give a variety of segments of the sequence. Further, once the sequence is cut with one or more restriction endonucleases, the resulting fragments can be "chewed back" further by use of exonucleases; or synthetic linkers can be added. In addition a double-stranded synthetic oligonucleotide fragment incorporating a multiple cloning site comprising several restriction endonuclease recognition sequences could be inserted into the translated region and the cloned segment would then have a more general utility. These operations all can be done by a person skilled in the art without undue experimentation. Thus, the scope of the subject invention encompasses all or part of the nucleotide sequences disclosed herein, provided that which is used enhances the level of expression or directs secretion in the prokaryotic expression/secretion system employed. Again, whether there is an enhancement of the expression level in a prokaryotic expression/secretion system can be readily ascertained by a person skilled in the art, using standard procedures described herein, without undue experimentation.

It should also be clear that the scope of the subject invention includes use of all or part of the disclosed NP949 structural gene sequence and all or part of the upstream untranslated DNA sequence of the NP949 promoter region not only to produce NP949 but also as part of an expression and/or secretion system to produce other useful proteins. In using the subject invention thusly, a person skilled in the art could readily determine whether all or only a part of the NP949 promoter and gene DNA would function best to give the high expression and/or secretion levels of desired protein. This determination, which can be made without undue experimentation, may well show that part or all of the 253 base pairs of the upstream untranslated sequence, along with all or part of the first 28 codons of the NP949 structural gene shown in Chart A, would give the highest expression level in a particular expression and/or secretion system designed for the production of a specific useful protein.

It should be readily evident to a person skilled in the art that the proteins produced by the NP949 expression system of the subject invention may be hybrid proteins, in that DNA from the expression/secretion system would be transcribed along with the particular protein gene DNA. These hybrid proteins would still retain the primary function(s) of the desired protein and, thus, could be used as the desired protein is used. If preferred, it is well within the skill of those in the art to further process the hybrid protein and recover the desired protein.

As is well known in the art, the nucleic acid sequence upstream of the structural gene specifies its promoter. Only certain of these nucleotides are important for promoter activity: those located 35 bases upstream, and those located 10 bases upstream of the site at which the mRNA is initiated. See, for example, Hawley, D. K. and McClure, W. R. (1983) Nucl. Acids Res. 11:2237–2255. The CAP protein (catabolite activator protein) is known to bind at certain promoter sites and to stimulate expression from that promoter: DeCrombrugghe, B., Busby, S. and Buc, H. (1984) Science 224:831–838. Nucleotide sequences interspersed between these sites may not contribute to expression activity. Thus certain bases can be changed without affecting this activity. Also, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | | |
|---|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Try) | TGG |
| Alanine (Ala) | GCI | Arginine (Arg) | WGZ |
| Tyrosine (Tyr) | TAK | Glycine (Gly) | GGL |
| Termination signal | TAJ | | |
| Termination signal | TGA | | |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T
QR = AG if S is T or C
J = A or G
K = T or C
L = A, T, C or G
M – A, C or T The above shows that a novel amino acid sequence can be prepared by more than one nucleotide sequence. Accordingly, the subject invention includes such equivalent nucleotide sequences. These functionally equivalent nucleotide sequences can be prepared by known synthetic procedures.

The work described herein was all done in conformity with physical and biological containment requirements specified in the NIH Guidelines.

CHART A

```
        SMA III
        CCCGGGGATC    GGATTTACTG    AAAATACCAT    TAAAAAATAT    CTACAATGCA   50

CTAACATCCA    GACAGTGACG    GTGCCTGTTC    CTGCGAAGTT    TTTACGTGCT   100

TCAAATGTAC    CGACTGGATT    GCTTAATGAA    ATGATTGCTT    ATCTCAACTC   150

GGAAGAACGC    ATCAATCATA    ATTTTTCAGA    ACTTTTGCTT    TTTTCTTGCC   200

TGTCTATTTT    TGCCGCATGC    AAAGGTTTCA    TTACACTATT    AACTAACGGT   250

GTGCTATCCG    TTTCTGGGAA    AGTGAGAAAT    ATTGTCAACA    TGAAGCCGGC   300

GCACCCATGG    AAGCTGAAAG    ATATTTGTGA    CTGCCTGTAC    ATCAGTGAAA   350

GCCGTGTGAA    GAAAAAACTT    AAGCAAGAGC    AAACGACATT    CTCACAGATT   400

CTTTTAGATG    CAAGAATGCA    GCACGCAAAA    AATTTGATAC    GCGTAGAAGG   450

TTCAGTCAAT    AAAATTGCCG    AACAATGTGG    TTATGCCAGT    ACATCTTATT   500

TTATTTATGC    GTTCCGCAAA    CATTTCGGCA    ACAGTCCGAA    GAGAGTTTCT   550
```

-continued
CHART A

```
                                                                        600
AAGGAGTACC    GTTGTCAAAG    TCACACGGGT    ATGAATACGG    GCAACACGAT

650
GAATGCTTTA    GCTATTTGAT    TATTTGCTAA    CGAGTAGTCA    ACCACACACG

700
CTGCGTAAGA    ATTAAATGGG    GCAGCCATTC    CCTGCCCCGC    GTTGTTTTTA

750
GGCGATATAT    TTATTGAAAT    AAATAAGTGA    CATCCATCAC    ATATTTATGC

NLA  III                                      800
ACTTGCATAA    CCTGTTGCAT    GATTATTTAT    GATCTCAATT    CTGCATTTTG

850
TCAGTAAAAT    GCAATAATTT    ATTAAATATC    AATAAATTAG    TTGTTTATCG

900
GCGAGAAATT    ACTTAATAGA    ACAGAAAGTA    ATGTCAACGC    TTTATGGACT

950
GTTTTTTCCC    TTTTTTTAGC    TAAATCTGCT    ATCTCTTTAT    GTGACTAACT

1000
TCACTTACAT    CCACTTATTT    CTCTTCGTAA    AATTACTTTG    GAATTAAGTA

RBS    MBO II                                            1044
CAATAAGAAG    AGGAACATTT    ATG   AAG   TCT   GCA   TTA   AAG   AAA   AGT
                            Met   Lys   Ser   Ala   Leu   Lys   Lys   Ser
```

|     |     |     |     |     | ECO RV |     |     |     |     |     |     | 1086 |
| --- | --- | --- | --- | --- | --- | --- | --- | --- | --- | --- | --- | --- |
| GTC | GTA | AGT | ACC | TCG | ATA | TCT | TTG | ATA | CTG | GCA | TCT | GGT ATG |
| Val | Val | Ser | Thr | Ser | Ile | Ser | Leu | Ile | Leu | Ala | Ser | Gly Met |

| SFANI |     |     |     |     | NLA III |     |     |     |     |     |     | 1128 |
| --- | --- | --- | --- | --- | --- | --- | --- | --- | --- | --- | --- | --- |
| GCT | GCA | TTT | GCT | GCT | CAT | GCG | GCA | GAT | GAT | GTA | AAG | CTG AAA |
| Ala | Ala | Phe | Ala | Ala | His | Ala | Ala | Asp | Asp | Val | Lys | Leu Lys |

|     |     |     |     |     |     |     | DDE I |     |     |     |     | 1170 |
| --- | --- | --- | --- | --- | --- | --- | --- | --- | --- | --- | --- | --- |
| GCA | ACC | AAA | ACA | AAC | GTT | GCT | TTC | TCA | GAC | TTT | ACG | CCG ACA |
| Ala | Thr | Lys | Thr | Asn | Val | Ala | Phe | Ser | Asp | Phe | Thr | Pro Thr |

|     |     |     |     |     |     |     |     | SSP I |     |     |     | 1212 |
| --- | --- | --- | --- | --- | --- | --- | --- | --- | --- | --- | --- | --- |
| GAA | TAC | AGT | ACC | AAA | GGA | AAG | CCA | AAT | ATT | ATC | GTA | CTG ACC |
| Glu | Tyr | Ser | Thr | Lys | Gly | Lys | Pro | Asn | Ile | Ile | Val | Leu Thr |

|     |     |     |     |     |     |     |     |     |     |     |     | 1254 |
| --- | --- | --- | --- | --- | --- | --- | --- | --- | --- | --- | --- | --- |
| ATG | GAT | GAT | CTT | GGT | TAT | GGA | CAA | CTT | CCT | TTT | GAT | AAG GGA |
| Met | Asp | Asp | Leu | Gly | Tyr | Gly | Gln | Leu | Pro | Phe | Asp | Lys Gly |

|     |     |     |     |     |     |     |     |     |     |     |     | 1296 |
| --- | --- | --- | --- | --- | --- | --- | --- | --- | --- | --- | --- | --- |
| TCT | TTT | GAC | CCA | AAA | ACA | ATG | GAA | AAT | CGT | GAA | GTT | GTC GAT |
| Ser | Phe | Asp | Pro | Lys | Thr | Met | Glu | Asn | Arg | Glu | Val | Val Asp |

|     |     |     |     |     |     |     |     |     |     |     |     | 1338 |
| --- | --- | --- | --- | --- | --- | --- | --- | --- | --- | --- | --- | --- |
| ACC | TAC | AAA | ATA | GGG | ATA | GAT | AAA | GCC | ATT | GAA | GCT | GCA CAA |
| Thr | Tyr | Lys | Ile | Gly | Ile | Asp | Lys | Ala | Ile | Glu | Ala | Ala Gln |

|     |     |     |     |     |     |     |     |     |     |     |     | 1380 |
| --- | --- | --- | --- | --- | --- | --- | --- | --- | --- | --- | --- | --- |
| AAA | TCA | ACG | CCG | ACG | CTC | CTT | TCA | TTA | ATG | GAT | GAA | GGC GTA |
| Lys | Ser | Thr | Pro | Thr | Leu | Leu | Ser | Leu | Met | Asp | Glu | Gly Val |

|     |     |     |     |     |     |     |     |     |     |     |     | 1422 |
| --- | --- | --- | --- | --- | --- | --- | --- | --- | --- | --- | --- | --- |
| CGT | TTT | ACT | AAC | GGC | TAT | GTG | GCA | CAC | GGT | GTT | TCC | GGC CCC |
| Arg | Phe | Thr | Asn | Gly | Tyr | Val | Ala | His | Gly | Val | Ser | Gly Pro |

|     |     |     |     |     |     |     |     |     |     |     |     | 1464 |
| --- | --- | --- | --- | --- | --- | --- | --- | --- | --- | --- | --- | --- |
| TCC | CGC | GCC | GCA | ATA | ATG | ACC | GGT | CGA | GCT | CCC | GCC | CGC TTT |
| Ser | Arg | Ala | Ala | Ile | Met | Thr | Gly | Arg | Ala | Pro | Ala | Arg Phe |

|     |     |     |     |     |     |     |     |     |     |     |     | 1506 |
| --- | --- | --- | --- | --- | --- | --- | --- | --- | --- | --- | --- | --- |
| GGT | GTC | TAT | TCC | AAT | ACC | GAT | GCT | CAG | GAT | GGT | ATT | CCG CTA |
| Gly | Val | Tyr | Ser | Asn | Thr | Asp | Ala | Gln | Asp | Gly | Ile | Pro Leu |

|     |     |     |     |     |     |     |     |     |     |     |     | 1548 |
| --- | --- | --- | --- | --- | --- | --- | --- | --- | --- | --- | --- | --- |
| ACA | GAA | ACT | TTC | TTG | CCT | GAA | TTA | TTC | CAG | AAT | CAT | GGT TAT |
| Thr | Glu | Thr | Phe | Leu | Pro | Glu | Leu | Phe | Gln | Asn | His | Gly Tyr |

PST i                                                                  1590

-continued
CHART A

| TAC | ACT | GCA | GCA | GTA | GGT | AAA | TGG | CAC | TTG | TCA | AAA | ATC | AGT |
| Tyr | Thr | Ala | Ala | Val | Gly | Lys | Trp | His | Leu | Ser | Lys | Ile | Ser |

| | | | | | | | | | | | | | 1632 |
| AAT | GTG | CCG | GTA | CCG | GAA | GAT | AAA | CAA | ACG | CGT | GAC | TAT | CAT |
| Asn | Val | Pro | Val | Pro | Glu | Asp | Lys | Gln | Thr | Arg | Asp | Tyr | His |

| | | | | | | | | | | | | | 1674 |
| GAC | AAC | TTC | ACC | ACA | TTT | TCT | GCG | GAA | GAA | TGG | CAA | CCT | CAA |
| Asp | Asn | Phe | Thr | Thr | Phe | Ser | Ala | Glu | Glu | Trp | Gln | Pro | Gln |

| | | | | | | | | | | PST I | | 1716 |
| AAC | CGT | GGC | TTT | GAT | TAC | TTT | ATG | GGA | TTC | CAC | GCT | GCA | GGA |
| Asn | Arg | Gly | Phe | Asp | Tyr | Phe | Met | Gly | Phe | His | Ala | Ala | Gly |

| | | | | | | | | | | | | | 1758 |
| ACG | GCA | TAT | TAC | AAC | TCC | CTT | CAC | TGT | TCA | AAA | ATC | GTG | AAC |
| Thr | Ala | Tyr | Tyr | Asn | Ser | Leu | His | Cys | Ser | Lys | Ile | Val | Asn |

| | | | | 1773 | | | | | | | | | |
| GTG | TCC | CGC | AAA | GGT | | | | | | | | | |
| Val | Ser | Arg | Lys | Gly | | | | | | | | | |

Chart B

```
                NLAIII                      DPNI
                CAT      GATTATTTAT         GATCTCAATT        CTGCATTTTG

TCAGTAAAAT    GCAATAATTT   ATTAAATATC     AATAAATTAG        TTGTTTATCG

HINCII
  GCGAGAAATT    ACTTAATAGA   ACAGAAAGTA     ATGTCAACGC        TTTATGGACT

ALUI                                          MAE3
  GTTTTTTCCC    TTTTTTTAGC   TAAATCTGCT     ATCTCTTTAT        GTGACTAACT

PFLMI                                         RSAI
  TCACTTACAT    CCACTTATTT   CTCTTCGTAA     AATTACTTTG        GAATTAAGTA

RBS   MBOII
  CAATAAGAAG    AGGAACATTT   ATG  AAG  TCT  GCA  TTA  AAG  AAA  AGT
                             Met  Lys  Ser  Ala  Leu  Lys  Lys  Ser

RBAI MNLI  TAQI    ECORV
  GTC GTA  AGT  ACC   TCG ATA TCT  TTG ATA CTG GCA TCT GGT ATG
  Val Val  Ser  Thr   Ser Ile Ser  Leu Ile Leu Ala Ser Gly Met

SFANI           FNU4HI      NLAIII
  GCT GCA  TTT   GCT GCT      CAT  G
  Ala Ala  Phe   Ala Ala      His
```

We claim:
1. A DNA sequence which is capable of enhancing the expression or secretion of a protein in a prokaryotic host wherein said DNA sequence is selected from the group consisting of:

(A)

| CCCGGGGATC | GGATTTACTG | AAAATACCAT |
| | | 50 |
| TAAAAAATAT | CTACAATGCA | CTAACATCCA |
| GACAGTGACG | GTGCCTGTTC | CTGCGAAGTT |
| 100 | | |
| TTTACGTGCT | TCAAATGTAC | CGACTGGATT |
| | | 150 |
| GCTTAATGAA | ATGATTGCTT | ATCTCAACTC |
| GGAAGAACGC | ATCAATCATA | ATTTTTCAGA |
| | 200 | |
| ACTTTTGCTT | TTTTCTTGCC | TGTCTATTTT |
| TGCCGCATGC | AAAGGTTTCA | TTACACTATT |
| | | 250 |
| AACTAACGGT | GTGCTATCCG | TTTCTGGGAA |
| | | 300 |
| AGTGAGAAAT | ATTGTCAACA | TGAAGCCGGC |
| GCACCCATGG | AAGCTGAAAG | ATATTTGTGA |
| | 350 | |
| CTGCCTGTAC | ATCAGTGAAA | GCCTGTTGAA |
| GAAAAAACTT | AAGCAAGAGC | AAACGACATT |
| | 400 | |
| CTCACAGATT | CTTTTAGATG | CAAGAATGCA |
| | | 450 |
| GCACGCAAAA | AATTTGATAC | GCGTAGAAGG |
| TTCAGTCAAT | AAAATTGCCG | AACAATGTGG |
| | | 500 |
| TTATGCCAGT | ACATCTTATT | TTATTTATGC |
| GTTCCGCAAA | CATTTCGGCA | ACAGTCCGAA |
| | 550 | |

```
                          -continued
GAGAGTTTCT    AAGGAGTACC    GTTGTCAAAG

600
TCACACGGGT    ATGAATACGG    GCAACACGAT

GAATGCTTTA    GCTATTTGAT    TATTTGCTAA

650
CGAGTAGTCA    ACCACACACG    CTGCGTAAGA

ATTAAATGGG    GCAGCCATTC    CCTGCCCCGC

700
GTTGTTTTTA    GGCGATATAT    TTATTGAAAT

750
AAATAAGTGA    CATCCATCAC    ATATTTATGC

ACTTGCATAA    CCTGTTGCAT    GATTATTTAT

800
GATCTCAATT    CTGCATTTTG    TCAGTAAAAT

GCAATAATTT    ATTAAATATC    AATAAATTAG

850
TTGTTTATCG    GCGAGAAATT    ACTTAATAGA

900
ACAGAAAGTA    ATGTCAACGC    TTTATGGACT

GTTTTTTCCC    TTTTTTTAGC    TAAATCTGCT

950
ATCTCTTTAT    GTGACTAACT    TCACTTACAT

CCACTTATTT    CTCTTCGTAA    AATTACTTTG

1000
GAATTAAGTA    CAATAAGAAG    AGGAACATTT

1050
ATGAAGTCTG    CATTAAAGAA    AAGTGTCGTA

AGTACCTCGA    TATCTTTGAT    ACTGGCATCT

1100
GGTATGGCTG    CATTTGCTGC    TCATGCGGCA

GATGATGTAA    AGCTGAAAGC    AACCAAAACA

1150
AACGTTGCTT    TCTCAGACTT    TACGCCGACA

1200
GAATACAGTA    CCAAAGGAAA    GCCAAATATT

ATCGTACTGA    CCATGGATGA    TCTTGGTTAT

1250
GGACAACTTC    CTTTTGATAA    GGGATCTTTT

GACCCAAAAA    CAATGGAAAA    TCGTGAAGTT

1300
GTCGATACCT    ACAAAATAGG    GATAGATAAA

1350
GCCATTGAAG    CTGCACAAAA    ATCAACGCCG

ACGCTCCTTT    CATTAATGGA    TGAAGGCGTA

1400
CGTTTTACTA    ACGGCTATGT    GGCACACGGT

GTTTCCGGCC    CCTCCCGCGC    CGCAATAATG

1450
ACCGGTCGAG    CTCCCGCCCG    CTTTGGTGTC

1500
TATTCCAATA    CCGATGCTCA    GGATGGTATT
```

```
                          -continued
CCGCTAACAG    AAACTTTCTT    GCCTGAATTA

1550
TTCCAGAATC    ATGGTTATTA    CACTGCAGCA

GTAGGTAAAT    GGCACTTGTC    AAAAATCAGT

1600
AATGTGCCGG    TACCGGAAGA    TAAACAAACG

1650
CGTGACTATC    ATGACAACTT    CACCACATTT

TCTGCGGAAG    AATGGCAACC    TCAAAACCGT

1700
GGCTTTGATT    ACTTTATGGG    ATTCCACGCT

GCAGGAACGG    CATATTACAA    CTCCCTTCAC

1750
TGTTCAAAAA    TCGTGAACGT    GTCCCGCAAA

1773
GGT;
```

```
                                         (B)
                          CAT    GATTATTTAT

800
GATCTCAATT    CTGCATTTTG    TCAGTAAAAT

GCAATAATTT    ATTAAATATC    AATAAATTAG

850
TTGTTTATCG    GCGAGAAATT    ACTTAATAGA

900
ACAGAAAGTA    ATGTCAACGC    TTTATGGACT

GTTTTTTCCC    TTTTTTTAGC    TAAATCTGCT

950
ATCTCTTTAT    GTGACTAACT    TCACTTACAT

CCACTTATTT    CTCTTCGTAA    AATTACTTTG

1000
GAATTAAGTA    CAATAAGAAG    AGGAACATTT

1050
ATGAAGTCTG    CATTAAAGAA    AAGTGTCGTA

AGTACCTCGA    TATCTTTGAT    ACTGGCATCT

1100
GGTATGGCTG    CATTTGCTGC    TCATG;
```

```
                                         (C)
                          ATGAAGTCTG

1050
CATTAAAGAA    AAGTGTCGTA    AGTACCTCGA

TATCTTTGAT    ACTGGCATCT    GGTATGGCTG

CATTTGCT;
```

(D) DNA sequences wherein the non-coding region (nucleotides 1 through 1020 inclusive) of (D) is identical to the non-coding region of (A), said non-coding region of (A) consisting of nucleotides 1 through 1020 inclusive of (A), and the coding region (nucleotides 1021 through 1773 inclusive) of (D) is any sequence that codes for the same amino acid sequence encoded by the coding region of (A), said coding region of (A) consisting of nucleotides 1021 through 1773 inclusive;

(E) DNA sequences wherein the non-coding region (nucleotides 768 through 1020 inclusive) of (E) is identical to the non-coding region of (B), said non-coding region of (B) consisting of nucleotides 768 through 1020 inclusive of (B), and the coding region (nucleotides 1021 through 1105 inclusive of (E) is any sequence that codes for the same amino acid sequence encoded by the coding region of (B), said coding region of (B) consisting of nucleotides 1021 through 1105 inclusive; and (F) DNA sequences encoding the same amino acid sequence encoded by the coding region of (C), said coding region of (C) consisting of nucleotides 1021 through 1098 inclusive.

2. The DNA sequence, according to claim 1, wherein said sequence is (A)

| | | | | 50 |
|---|---|---|---|---|
| CCCGGGGATC | GGATTTACTG | AAAATACCAT | TAAAAAATAT | CTACAATGCA |
| CTAACATCCA | GACAGTGACG | GTGCCTGTTC | CTGCGAAGTT | TTTACGTGCT |
| | | | | 100 |
| TCAAATGTAC | CGACTGGATT | GCTTAATGAA | ATGATTGCTT | ATCTCAACTC |
| | | | | 150 |
| GGAAGAACGC | ATCAATCATA | ATTTTTCAGA | ACTTTTGCTT | TTTTCTTGCC |
| | | | | 200 |
| TGTCTATTTT | TGCCGCATGC | AAAGGTTTCA | TTACACTATT | AACTAACGGT |
| | | | | 250 |
| GTGCTATCCG | TTTCTGGGAA | AGTGAGAAAT | ATTGTCAACA | TGAAGCCGGC |
| | | | | 300 |
| GCACCCATGG | AAGCTGAAAG | ATATTTGTGA | CTGCCTGTAC | ATCAGTGAAA |
| | | | | 350 |
| GCCGTGTGAA | GAAAAAACTT | AAGCAAGAGC | AAACGACATT | CTCACAGATT |
| | | | | 400 |
| CTTTTAGATG | CAAGAATGCA | GCACGCAAAA | AATTTGATAC | GCGTAGAAGG |
| | | | | 450 |
| TTCAGTCAAT | AAAATTGCCG | AACAATGTGG | TTATGCCAGT | ACATCTTATT |
| | | | | 500 |
| TTATTTATGC | GTTCCGCAAA | CATTTCGGCA | ACAGTCCGAA | GAGAGTTTCT |
| | | | | 550 |
| AAGGAGTACC | GTTGTCAAAG | TCACACGGGT | ATGAATACGG | GCAACACGAT |
| | | | | 600 |
| GAATGCTTTA | GCTATTTGAT | TATTTGCTAA | CGAGTAGTCA | ACCACACACG |
| | | | | 650 |
| CTGCGTAAGA | ATTAAATGGG | GCAGCCATTC | CCTGCCCCGC | GTTGTTTTA |
| | | | | 700 |
| GGCGATATAT | TTATTGAAAT | AAATAAGTGA | CATCCATCAC | ATATTTATGC |
| | | | | 750 |
| ACTTGCATAA | CCTGTTGCAT | GATTATTTAT | GATCTCAATT | CTGCATTTTG |
| | | | | 800 |
| TCAGTAAAAT | GCAATAATTT | ATTAAATATC | AATAAATTAG | TTGTTTATCG |
| | | | | 850 |
| GCGAGAAATT | ACTTAATAGA | ACAGAAAGTA | ATGTCAACGC | TTTATGGACT |
| | | | | 900 |
| GTTTTTTCCC | TTTTTTTAGC | TAAATCTGCT | ATCTCTTTAT | GTGACTAACT |
| | | | | 950 |
| TCACTTACAT | CCACTTATTT | CTCTTCGTAA | AATTACTTTG | GAATTAAGTA |
| | | | | 1000 |
| CAATAAGAAG | AGGAACATTT | ATGAAGTCTG | CATTAAAGAA | AAGTGTCGTA |
| | | | | 1050 |
| AGTACCTCGA | TATCTTTGAT | ACTGGCATCT | GGTATGGCTG | CATTTGCTGC |
| | | | | 1100 |
| TCATGCGGCA | GATGATGTAA | AGCTGAAAGC | AACCAAAACA | AACGTTGCTT |
| | | | | 1150 |
| TCTCAGACTT | TACGCCGACA | GAATACAGTA | CCAAAGGAAA | GCCAAATATT |
| | | | | 1200 |
| | | | | 1250 |

```
ATCGTACTGA    CCATGGATGA    TCTTGGTTAT    GGACAACTTC    CTTTTGATAA
                                                        1300
GGGATCTTTT    GACCCAAAAA    CAATGGAAAA    TCGTGAAGTT    GTCGATACCT
                                                        1350
ACAAAATAGG    GATAGATAAA    GCCATTGAAG    CTGCACAAAA    ATCAACGCCG
                                                        1400
ACGCTCCTTT    CATTAATGGA    TGAAGGCGTA    CGTTTTACTA    ACGGCTATGT
                                                        1450
GGCACACGGT    GTTTCCGGCC    CCTCCCGCGC    CGCAATAATG    ACCGGTCGAG
                                                        1500
CTCCCGCCCG    CTTTGGTGTC    TATTCCAATA    CCGATGCTCA    GGATGGTATT
                                                        1550
CCGCTAACAG    AAACTTTCTT    GCCTGAATTA    TTCCAGAATC    ATGGTTATTA
                                                        1600
CACTGCAGCA    GTAGGTAAAT    GGCACTTGTC    AAAAATCAGT    AATGTGCCGG
                                                        1650
TACCGGAAGA    TAAACAAACG    CGTGACTATC    ATGACAACTT    CACCACATTT
                                                        1700
TCTGCGGAAG    AATGGCAACC    TCAAAACCGT    GGCTTTGATT    ACTTTATGGG
                                                        1750
ATTCCACGCT    GCAGGAACGG    CATATTACAA    CTCCCTTCAC    TGTTCAAAAA
                          177
TCGTGAACGT    GTCCCGCAAA    GGT.
```

3. The DNA sequence, according to claim 1, wherein said sequence is

5. A DNA sequence coding for a protein having an amino acid sequence selected from the group consisting

```
                                                 800   (B)
              CAT           GATTATTTAT    GATCTCAATT    CTGCATTTTG
                                                        850
TCAGTAAAAT    GCAATAATTT    ATTAAATATC    AATAAATTAG    TTGTTTATCG
                                                        900
GCGAGAAATT    ACTTAATAGA    ACAGAAAGTA    ATGTCAACGC    TTTATGGACT
                                                        950
GTTTTTTCCC   TTTTTTTAGC    TAAATCTGCT    ATCTCTTTAT    GTGACTAACT
                                                        1000
TCACTTACAT    CCACTTATTT    CTCTTCGTAA    AATTACTTTG    GAATTAAGTA
                                                        1050
CAATAAGAAG    AGGAACATTT    ATGAAGTCTG    CATTAAAGAA    AAGTGTCGTA
                                                        1100
AGTACCTCGA    TATCTTTGAT    ACTGGCATCT    GGTATGGCTG    CATTTGCTGC
TCATG.
```

4. The DNA sequence, according to claim 1, wherein said sequence is

```
                                                 1050  (C)
              ATGAAGTCTG    CATTAAAGAA    AAGTGTCGTA
ACTACCTCGA    TATCTTTGAT    ACTGGCATCT    GGTATGGCTG    CATTTGCT.
``` of

```
         Met  Lys  Ser  Ala  Leu  Lys  Lys  Ser  Val  Val  Ser  Thr  Ser  Ile   (A)
         Ser  Leu  Ile  Leu  Ala  Ser  Gly  Met  Ala  Ala  Phe  Ala  Ala  His
         Ala  Ala  Asp  Asp  Val  Lys  Leu  Lys  Ala  Thr  Lys  Thr  Asn  Val
         Ala  Phe  Ser  Asp  Phe  Thr  Pro  Thr  Glu  Tyr  Ser  Thr  Lys  Gly
         Lys  Pro  Asn  Ile  Ile  Val  Leu  Thr  Met  Asp  Asp  Leu  Gly  Tyr
         Gly  Gln  Leu  Pro  Phe  Asp  Lys  Gly  Ser  Phe  Asp  Pro  Lys  Thr
         Met  Glu  Asn  Arg  Glu  Val  Val  Asp  Thr  Tyr  Lys  Ile  Gly  Ile
         Asp  Lys  Ala  Ile  Glu  Ala  Ala  Gln  Lys  Ser  Thr  Pro  Thr  Leu
         Leu  Ser  Leu  Met  Asp  Glu  Gly  Val  Arg  Phe  Thr  Asn  Gly  Tyr
```

| Val | Ala | His | Gly | Val | Ser | Gly | Pro | Ser | Arg | Ala | Ala | Ile | Met | |
| Thr | Gly | Arg | Ala | Pro | Ala | Arg | Phe | Gly | Val | Tyr | Ser | Asn | Thr | |
| Asp | Ala | Gln | Asp | Gly | Ile | Pro | Leu | Thr | Glu | Thr | Phe | Leu | Pro | |
| Glu | Leu | Phe | Gln | Asn | His | Gly | Tyr | Tyr | Thr | Ala | Ala | Val | Gly | |
| Lys | Trp | His | Leu | Ser | Lys | Ile | Ser | Asn | Val | Pro | Val | Pro | Glu | |
| Asp | Lys | Gln | Thr | Arg | Asp | Tyr | His | Gln | Phe | Thr | Thr | Phe | | |
| Ser | Ala | Glu | Glu | Trp | Gln | Pro | Gln | Asn | Arg | Gly | Phe | Asp | Tyr | |
| Phe | Met | Gly | Phe | His | Ala | Ala | Gly | Thr | Ala | Tyr | Tyr | Asn | Ser | |
| Leu | His | Cys | Ser | Lys | Ile | Val | Asn | Val | Ser | Arg | Lys | Gly; | | |
| Met | Lys | Ser | Ala | Leu | Lys | Lys | Ser | Val | Val | Ser | Thr | Ser | Ile | (B) |
| Ser | Leu | Ile | Leu | Ala | Ser | Gly | Met | Ala | Ala | Phe | Ala | Ala | His; and | |
| Met | Lys | Ser | Ala | Leu | Lys | Lys | Ser | Val | Val | Ser | Thr | Ser | Ile | (C) |
| Ser | Leu | Ile | Leu | Ala | Ser | Gly | Met | Ala | Ala | Phe | Ala | | | |

6. A DNA transfer vector comprising a DNA sequence which is capable of enhancing the expression or secretion of a protein in a prokaryotic host wherein said DNA sequence is selected from the group consisting of:

(A)
```
             CCCGGGGATC  GGATTTACTG  AAAATACCAT
                                   50
             TAAAAAATAT  CTACAATGCA  CTAACATCCA
             GACAGTGACG  GTGCCTGTTC  CTGCGAAGTT
                    100
             TTTACGTGCT  TCAAATGTAC  CGACTGGATT
                                  150
             GCTTAATGAA  ATGATTGCTT  ATCTCAACTC
             GGAAGAACGC  ATCAATCATA  ATTTTTCAGA
                              200
             ACTTTTGCTT  TTTTCTTGCC  TGTCTATTTT
             TGCCGCATGC  AAAGGTTTCA  TTACACTATT
              250
             AACTAACGGT  GTGCTATCCG  TTTCTGGGAA
                                  300
             AGTGAGAAAT  ATTGTCAACA  TGAAGCCGGC
             GCACCCATGG  AAGCTGAAAG  ATATTTGTGA
                         350
             CTGCCTGTAC  ATCAGTGAAA  GCCTGTTGAA
             GAAAAAACTT  AAGCAAGAGC  AAACGACATT
              400
             CTCACAGATT  CTTTTAGATG  CAAGAATGCA
                                  450
             GCACGCAAAA  AATTTGATAC  GCGTAGAAGG
             TTCAGTCAAT  AAAATTGCCG  AACAATGTGG
                         500
             TTATGCCAGT  ACATCTTATT  TTATTTATGC
             GTTCCGCAAA  CATTTCGGCA  ACAGTCCGAA
              550
             GAGAGTTTCT  AAGGAGTACC  GTTGTCAAAG
                                  600
             TCACACGGGT  ATGAATACGG  GCAACACGAT
             GAATGCTTTA  GCTATTGAT  TATTTGCTAA
                         650
             CGAGTAGTCA  ACCACACACG  CTGCGTAAGA
             ATTAAATGGG  GCAGCCATTC  CCTGCCCCGC
                    700
             GTTGTTTTTA  GGCGATATAT  TTATTGAAAT
                                  750
             AAATAAGTGA  CATCCATCAC  ATATTTATGC
             ACTTGCATAA  CCTGTTGCAT  GATTATTTAT
                              800
             GATCTCAATT  CTGCATTTTG  TCAGTAAAAT
             GCAATAATTT  ATTAAATATC  AATAAATTAG
                    850
             TTGTTTATCG  GCGAGAAATT  ACTTAATAGA
                                  900
             ACAGAAAGTA  ATGTCAACGC  TTTATGGACT
             GTTTTTTCCC  TTTTTTTAGC  TAAATCTGCT
                              950
             ATCTCTTTAT  GTGACTAACT  TCACTTACAT
             CCACTTATTT  CTCTTCGTAA  AATTACTTTG
                    1000
             GAATTAAGTA  CAATAAGAAG  AGGAACATTT
                                  1050
             ATGAAGTCTG  CATTAAAGAA  AAGTGTCGTA
             AGTACCTCGA  TATCTTTGAT  ACTGGCATCT
                              1100
             GGTATGGCTG  CATTTGCTGC  TCATGCGGCA
             GATGATGTAA  AGCTGAAAGC  AACCAAAACA
                    1150
             AACGTTGCTT  TCTCAGACTT  TACGCCGACA
                                  1200
             GAATACAGTA  CCAAAGGAAA  GCCAAATATT
             ATCGTACTGA  CCATGGATGA  TCTTGGTTAT
                              1250
             GGACAACTTC  CTTTTGATAA  GGGATCTTTT
             GACCCAAAAA  CAATGGAAAA  TCGTGAAGTT
                    1300
             GTCGATACCT  ACAAAATAGG  GATAGATAAA
                                  1350
             GCCATTGAAG  CTGCACAAAA  ATCAACGCCG
             ACGCTCCTTT  CATTAATGGA  TGAAGGCGTA
                              1400
             CGTTTTACTA  ACGGCTATGT  GGCACACGGT
             GTTTCCGGCC  CCTCCCGCGC  CGCAATAATG
                    1450
             ACCGGTCGAG  CTCCCGCCCG  CTTTGGTGTC
```

| | | 1500 |
|---|---|---|
| TATTCCAATA | CCGATGCTCA | GGATGGTATT |
| CCGCTAACAG | AAACTTTCTT | GCCTGAATTA |
| | 1550 | |
| TTCCAGAATC | ATGGTTATTA | CACTGCAGCA |
| GTAGGTAAAT | GGCACTTGTC | AAAAATCAGT |
| 1600 | | |
| AATGTGCCGG | TACCGGAAGA | TAAACAAACG |
| | | 1650 |
| CGTGACTATC | ATGACAACTT | CACCACATTT |
| TCTGCGGAAG | AATGGCAACC | TCAAAACCGT |
| | 1700 | |
| GGCTTTGATT | ACTTTATGGG | ATTCCACGCT |
| GCAGGAACGG | CATATTACAA | CTCCCTTCAC |
| 1750 | | |
| TGTTCAAAAA | TCGTGAACGT | GTCCCGCAAA |
| 1773 | | |
| GGT; | | |

(B)

| | CAT | GATTATTTAT |
|---|---|---|
| | 800 | |
| GATCTCAATT | CTGCATTTTG | TCAGTAAAAT |
| GCAATAATTT | ATTAAATATC | AATAAATTAG |
| 850 | | |
| TTGTTTATCG | GCGAGAAATT | ACTTAATAGA |
| | | 900 |
| ACAGAAAGTA | ATGTCAACGC | TTTATGGACT |
| GTTTTTTCCC | TTTTTTTAGC | TAAATCTGCT |
| | 950 | |
| ATCTCTTTAT | GTGACTAACT | TCACTTACAT |
| CCACTTATTT | CTCTTCGTAA | AATTACTTTG |
| 1000 | | |
| GAATTAAGTA | CAATAAGAAG | AGGAACATTT |
| | | 1050 |
| ATGAAGTCTG | CATTAAAGAA | AAGTGTCGTA |
| AGTACCTCGA | TATCTTTGAT | ACTGGCATCT |
| | 1100 | |
| GGTATGGCTG | CATTTGCTGC | TCATG; |

(C)

| | | ATGAAGTCTG |
|---|---|---|
| | 1050 | |
| CATTAAAGAA | AAGTGTCGTA | AGTACCTCGA |
| TATCTTTGAT | ACTGGCATCT | GGTATGGCTG |
| CATTTGCT; | | |

(D) DNA sequences wherein the non-coding region (nucleotides 1 through 1020 inclusive) of (D) is identical to the non-coding region of (A), said non-coding region of (A) consisting of nucleotides 1 through 1020 inclusive of (A), and the coding region (nucleotides 1021 through 1773 inclusive of (D) is any sequence that codes for the same amino acid sequence encoded by the coding region of (A), said coding region of (A) consisting of nucleotides 1020 through 1773 inclusive;

(E) DNA sequences wherein the non-coding region (nucleotides 768 through 1020 inclusive) of (E) is identical to the non-coding region of (B), said non-coding region of (B) consisting of nucleotides 768 through 1020 inclusive of (B), and the coding region (nucleotides 1021 through 1105 inclusive) of (E) is any sequence that codes for the same amino acid sequence encoded by the coding region of (B), said coding region of (B) consisting of nucleotides 1021 through 1105 inclusive; and (F) DNA sequences encoding the same amino acid sequence encoded by the coding region of (C), said coding region of (C) consisting of nucleotides 1021 through 1098 inclusive.

7. The transfer vector, according to claim 6, wherein said transfer vector is selected from the group consisting of pNP949 and pNP949H.

8. A prokaryotic host transformed by the DNA transfer vector of claim 6.

9. The prokaryotic host, according to claim 8, wherein said host is *Escherichia coli*.

10. The prokaryotic host, according to claim 9, wherein said host is selected from the group consisting of *Escherichia coli* KL386(pNP949) and *Escherichia coli* KL386(PHP949H).

11. A process for enhancing the expression or secretion of a protein in a prokaryotic host, said process comprising culturing a prokaryotic host comprising the DNA transfer vector of claim 6.

12. The process, according to claim 11, wherein said transfer vector comprises DNA having the following nucleotide sequence:

(A)

| | | | | 50 |
|---|---|---|---|---|
| CCCGGGGATC | GGATTTACTG | AAAATACCAT | TAAAAAATAT | CTACAATGCA |
| | | | | 100 |
| CTAACATCCA | GACAGTGACG | GTGCCTGTTC | CTGCGAAGTT | TTTACGTGCT |
| | | | | 150 |
| TCAAATGTAC | CGACTGGATT | GCTTAATGAA | ATGATTGCTT | ATCTCAACTC |
| | | | | 200 |
| GGAAGAACGC | ATCAATCATA | ATTTTTCAGA | ACTTTTGCTT | TTTTCTTGCC |
| | | | | 250 |
| TGTCTATTTT | TGCCGCATGC | AAAGGTTTCA | TTACACTATT | AACTAACGGT |
| | | | | 300 |
| GTGCTATCCG | TTTCTGGGAA | AGTGAGAAAT | ATTGTCAACA | TGAAGCCGGC |

```
GCACCCATGG  AAGCTGAAAG  ATATTTGTGA  CTGCCTGTAC  ATCAGTGAAA   350
GCCGTGTGAA  GAAAAAACTT  AAGCAAGAGC  AAACGACATT  CTCACAGATT   400
CTTTTAGATG  CAAGAATGCA  GCACGCAAAA  AATTTGATAC  GCGTAGAAGG   450
TTCAGTCAAT  AAAATTGCCG  AACAATGTGG  TTATGCCAGT  ACATCTTATT   500
TTATTTATGC  GTTCCGCAAA  CATTTCGGCA  ACAGTCCGAA  GAGAGTTTCT   550
AAGGAGTACC  GTTGTCAAAG  TCACACGGGT  ATGAATACGG  GCAACACGAT   600
GAATGCTTTA  GCTATTTGAT  TATTTGCTAA  CGAGTAGTCA  ACCACACACG   650
CTGCGTAAGA  ATTAAATGGG  GCAGCCATTC  CCTGCCCCGC  GTTGTTTTTA   700
GGCGATATAT  TTATTGAAAT  AAATAAGTGA  CATCCATCAC  ATATTTATGC   750
ACTTGCATAA  CCTGTTGCAT  GATTATTTAT  GATCTCAATT  CTGCATTTTG   800
TCAGTAAAAT  GCAATAATTT  ATTAAATATC  AATAAATTAG  TTGTTTATCG   850
GCGAGAAATT  ACTAATAGA   ACAGAAAGTA  ATGTCAACGC  TTTATGGACT   900
GTTTTTTCCC  TTTTTTTAGC  TAAATCTGCT  ATCTCTTTAT  GTGACTAACT   950
TCACTTACAT  CCACTTATTT  CTCTTCGTAA  AATTACTTTG  GAATTAAGTA  1000
CAATAAGAAG  AGGAACATTT  ATGAAGTCTG  CATTAAAGAA  AAGTGTCGTA  1050
AGTACCTCGA  TATCTTTGAT  ACTGGCATCT  GGTATGGCTG  CATTTGCTGC  1100
TCATGCGGCA  GATGATGTAA  AGCTGAAAGC  AACCAAAACA  AACGTTGCTT  1150
TCTCAGACTT  TACGCCGACA  GAATACAGTA  CCAAAGGAAA  GCCAAATATT  1200
ATCGTACTGA  CCATGGATGA  TCTTGGTTAT  GGACAACTTC  CTTTTGATAA  1250
GGGATCTTTT  GACCCAAAAA  CAATGGAAAA  TCGTGAAGTT  GTCGATACCT  1300
ACAAAATAGG  GATAGATAAA  GCCATTGAAG  CTGCACAAAA  ATCAACGCCG  1350
ACGCTCCTTT  CATTAATGGA  TGAAGGCGTA  CGTTTTACTA  ACGGCTATGT  1400
GGCACACGGT  GTTTCCGGCC  CCTCCCGCGC  CGCAATAATG  ACCGGTCGAG  1450
CTCCCGCCCG  CTTTGGTGTC  TATTCCAATA  CCGATGCTCA  GGATGGTATT  1500
CCGCTAACAG  AAACTTTCTT  GCCTGAATTA  TTCCAGAATC  ATGGTTATTA  1550
CACTGCAGCA  GTAGGTAAAT  GGCACTTGTC  AAAAATCAGT  AATGTGCCGG  1600
TACCGGAAGA  TAAACAAACG  CGTGACTATC  ATGACAACTT  CACCACATTT  1650
TCTGCGGAAG  AATGGCAACC  TCAAAACCGT  GGCTTTGATT  ACTTTATGGG  1700
```

|  |  |  |  | 1750 |
|---|---|---|---|---|
| ATTCCACGCT | GCAGGAACGG | CATATTACAA | CTCCCTTCAC | TGTTCAAAAA |
| TCGTGAACGT | GTCCCGCAAA | 177<br>GGT. | | |

13. The process, according to claim 11, wherein said transfer vector comprises DNA having the following nucleotide sequence:

|  |  |  | 800 | (B) |
|---|---|---|---|---|
|  | CAT | GATTATTTAT | GATCTCAATT | CTGCATTTTG |
| TCAGTAAAAT | GCAATAATTT | ATTAAATATC | AATAAATTAG | 850<br>TTGTTTATCG |
| GCGAGAAATT | ACTTAATAGA | ACAGAAAGTA | ATGTCAACGC | 900<br>TTTATGGACT |
| GTTTTTTCCC | TTTTTTTAGC | TAAATCTGCT | ATCTCTTTAT | 950<br>GTGACTAACT |
| TCACTTACAT | CCACTTATTT | CTCTTCGTAA | AATTACTTTG | 1000<br>GAATTAAGTA |
| CAATAAGAAG | AGGAACATTT | ATGAAGTCTG | CATTAAAGAA | 1050<br>AAGTGTCGTA |
| AGTACCTCGA | TATCTTTGAT | ACTGGCATCT | GGTATGGCTG | 1100<br>CATTTGCTGC |
| TCATG. | | | | |

14. The process, according to claim 11, wherein said transfer vector comprises DNA having the following nucleotide sequence:

|  |  |  | 1050 | (C) |
|---|---|---|---|---|
|  |  | ATGAAGTCTG | CATTAAAGAA | AAGTGTCGTA |
| ACTACCTCGA | TATCTTTGAT | ACTGGCATCT | GGTATGGCTG | CATTTGCT. |

15. The process, according to claim 11, wherein the prokaryotic host is *Es herichia coli*.

16. The process, according to claim 15, wherein said prokaryotic host is *Escherichia coli* KL386(pNP949) or *Escherichia coli* KL386(pNP949H).

* * * * *

UNITED STATES PATENT AND TRADEMARK OFFICE
CERTIFICATE OF CORRECTION

PATENT NO.   :   5,047,334

DATED        :   Sept. 10, 1991

INVENTOR(S)  :   Joan Petro, Jennifer Jackson, and Scott Putney

It is certified that error appears in the above-identified patent and that said Letters Patent is hereby corrected as shown below:

Column 6 line 42: "libray" should read --library--.
Column 6 line 43: "DNa" should read --DNA--.
Column 10 line 27: "fragement" should read --fragment--.
Column 11, chart A, line 1: "SMA III" should read --SMA I--.
Column 11, chart A, line 9: "GCCGTGTGAA" should read --GCCTGTTGAA--.
Column 13 line 50: "GCT" (amino acid 1450)should have --SST I-- inserted above.
Column 19 line 4: "inclusive of" should read --inclusive) of--.
Column 21 line 22: "177" should read --1773--.
Column 21, claim 4, line 4: "ACTACCTCGA" should read --AGTACCTCGA--.
Column 26, claim 6, line 16: "inclusive of" should read --inclusive) of--.
Column 26, claim 6, line 20: "1020" should read --1021--.
Column 26, claim 10, line 45: "KL386(PHP949H)" should read --KL386(pNP949H)--.
Column 27, claim 12, line 2: "GCCGTGTGAA" should read --GCCTGTTGAA--.
Column 29, claim 12, line 2: "177" should read --1773--.
Column 29, claim 14, line 6: "ACTACCTCGA" should read --AGTACCTCGA--.
Column 30, claim 15, line 9: "*Esherichia*" should read --*Escherichia*--.

Signed and Sealed this

Ninth Day of February, 1993

*Attest:*

STEPHEN G. KUNIN

*Attesting Officer*           *Acting Commissioner of Patents and Trademarks*